United States Patent [19] [11] 4,054,607
Matsuoka et al. [45] Oct. 18, 1977

[54] PROCESS FOR PREPARING ANISALDEHYDE

[75] Inventors: Manabu Matsuoka, Toyonaka; Hiroyasu Seko, Nara, both of Japan

[73] Assignee: Tanabe Seiyaku Co., Ltd., Osaka, Japan

[21] Appl. No.: 697,473

[22] Filed: June 18, 1976

[30] Foreign Application Priority Data

July 21, 1975 Japan .................................. 50-89552

[51] Int. Cl.$^2$ ............................................. C07C 45/00
[52] U.S. Cl. .................................. 260/600 R; 252/437
[58] Field of Search .............................. 260/599, 600

[56] References Cited

U.S. PATENT DOCUMENTS

| 1,909,355 | 5/1933 | Jaeger | 260/600 X |
| 3,946,067 | 3/1976 | Kwiatek et al. | 260/599 X |

*Primary Examiner*—Bernard Helfin
*Attorney, Agent, or Firm*—Bierman & Bierman

[57] ABSTRACT

Preparation of anisaldehyde by the oxidation of p-methoxytoluene in the vapor phase in the presence of a catalyst consisting of vanadium oxide, phosphorus oxide and potassium sulfate or a catalyst consisting of vanadium oxide, phosphorus oxide, potassium sulfate and copper oxide. The catalyst has excellent selectivity and, as a result, anisaldehyde is obtained in high yields. Further, the catalyst containing copper oxide has excellent durability.

6 Claims, No Drawings

PROCESS FOR PREPARING ANISALDEHYDE

BACKGROUND OF THE INVENTION

The present invention relates to the preparation of anisaldehyde, and more particularly to the preparation of anisaldehyde by the oxidation of p-methoxytoluene in the vapor phase in the presence of a novel catalyst.

It is known from Chemical Abstracts, Vol. 66, 2847u(1967), Chemical Abstracts, Vol. 74, 125060d(1971) and U.S.S.R. Pat. No. 360,844 that anisaldehyde is prepared by oxidizing p-methoxytoluene in the liquid phase in the presence of a catalyst. However, it has never been known that p-methoxytoluene can be converted to anisaldehyde by oxidation in the vapor phase.

It is also known that a methyl group attached to an aromatic ring is converted to an aldehyde by oxidation in the vapor phase. For instance, it is known that an aromatic compound such as toluene ro xylene is converted to the corresponding aldehyde by oxidation in the vapor phase with a catalyst containing molybdenum as a main component or a catalyst consisting of vanadium oxide and phosphorus oxide. The present inventors have attempted to oxidize p-methoxytoluene in the vapor phase by employing a catalyst containing molybdenum as a main component or a catalyst consisting of vanadium oxide and phosphorus oxide. However, in case of the catalyst containing molybdenum, the catalyst does not show any catalytic activity with respect to p-methoxytoluene. Also, in case of the catalyst consisting of vanadium oxide and phosphorus oxide, p-methoxytoluene is oxidized to carbon dioxide and water in one step and anisaldehyde is not produced.

OBJECTS OF THE INVENTION

It is an object of the present invention to provide a novel catalyst useful in preparing anisaldehyde by oxidizing p-methoxytoluene in the vapor phase.

A further object of the invention is to provide a catalyst with a high degree of selectivity for use in preparing anisaldehyde by oxidizing p-methoxytoluene.

A still further object of the invention is to provide a catalyst with excellent durability for use in preparing anisaldehyde by oxidizing p-methoxytoluene.

Another object of the invention is to provide a process for preparing anisaldehyde in high yield by the oxidation of p-methoxytoluene in the vapor phase.

These and other objects of the invention will become apparent from the description hereinafter.

DETAILED DESCRIPTION

It has now been found that the above-mentioned objectives can be attained by the use of a catalyst consisting of vanadium oxide, phosphorus oxide and potassium sulfate. It has also been found that the presence of copper oxide in the catalyst extends the useful life thereof.

According to the present invention, anisaldehyde can be prepared with high selectivity and in high yields by the oxidation of p-methoxytoluene in the vapor phase by the use of a catalyst consisting of vanadium oxide, phosphorus oxide and potassium sulfate or a catalyst consisting of vanadium oxide, phosphorus oxide, potassium sulfate and copper oxide. The preparation can be effectively carried out over a long period of time even if the reaction is effected under a high gas concentration of the starting material; for example, p-methoxytoluene gas concentration of about 100 g./m.$^3$ of air.

In the present invention, the preferable vanadium oxide is vanadium pentoxide and the preferable phosphorus oxide is diphosphorus pentoxide. Also, the preferable copper oxide is cupric oxide.

The catalyst employed in the oxidation of p-methoxytoluene in the vapor phase may be prepared in various ways. For instance, a phosphorus compound and potassium sulfate are dissolved in an aqueous solution containing a vanadium compound. If desired, a copper compound is also dissolved in the solution. These compounds may be supported on an inert carrier by dipping the carrier in the solution and then drying. When the amount of water present is great and sufficient amounts of the compounds can not be supported on the carrier by one dipping procedure, the procedures of dipping and drying are repeated. When the amount of water present is small, the metal compounds often do not completely dissolve in the water. In that case, the solution is evaporated once to dryness and, after grinding the solid matter to a powder, a small amount of water is added to the powder to form a slurry. The slurry is then supported on an inert carrier by sprinkling the slurry over the carrier previously heated or by the use of a known method. In this manner the compounds can be uniformly supported on the carrier. Then sintering is carried out in a stream of air at a temperature of about 550° to about 650° C. for a period of about 1 to about 18 hours. Thus, a catalyst substantially containing vanadium pentoxide, diphosphorus pentoxide and potassium sulfate or a catalyst substantially containing the above components and cupric oxide can be prepared.

Examples of the vanadium compound employed in preparing the catalyst of the invention are ammonium vanadate, vanadyl sulfate and vanadyl oxalate. Examples of the phosphorus compound employed in preparing the catalyst of the invention are phosphoric acid and ammonium phosphate. Examples of the copper compound employed in preparing the catalyst of the invention are copper nitrate, copper sulfate and copper chloride. According to the present invention, potassium hydroxide and sulfuric acid may be employed instead of potassium sulfate. The inert carriers usually employed are pumice, alumina, silicon carbide and silica. These inert carriers may be crystalline or amorphous, and may be employed in the form of a powder or mass. Granules having a particle size of about 0.3 mm. to about 10 mm. are especially suitable.

A catalyst prepared by supporting a mixture of vanadium pentoxide, diphosphorus pentoxide and potassium sulfate on the carrier may also be employed in the present invention. Preferably the sintering of the thus prepared catalyst is carried out. Although the catalytic activity of a catalyst not subjected to sintering is low at the initial stage of the reaction, it is gradually increased in the course of reaction and soon reaches the catalytic activity of a sintered catalyst. The arrangement of the molecules in a catalyst not subjected to the sintering is irregular. However, with increased activity as a result of use the arrangement of the molecules becomes regular. A sintered catalyst also shows the regular arrangement of the molecules. Therefore, it is presumed that the increased activity in both the sintered and unsintered catalysts is due to the regular arrangement of the molecules.

When the amount of potassium sulfate present is too high or too low, the desired anisaldehyde has a tendency to oxidize to the corresponding carboxylic acid, thus reducing the selectivity of the catalyst and the production of anisaldehyde. Therefore, the amount of potassium sulfate used should be between about 1.5 and about 2.5 moles per mole of vanadium oxide.

Copper oxide is employed in an amount of 0 to about 0.1 mole per mole of vanadium oxide. When the catalyst contains copper oxide, the life of the catalyst is remarkably prolonged because the transportation of oxygen in the catalyst becomes smoother and the catalytic oxidation reaction can be effected at a lower temperature. Although the activity of the catalyst not containing copper oxide was lowered to some extent when it was continuously employed for about one week, the catalyst containing copper oxide could be continuously used for about 1 month without lowering its catalytic activity.

The amount of phosphorus oxide used is from about 0.2 to about 0.8 mole per mole of vanadium oxide.

When preparing anisaldehyde by oxidizing p-methoxytoluene in the vapor phase with the catalyst of the present invention, any reaction apparatus of conventional design which has been generally used in known vapor phase reaction may be used, and the catalytic reaction is carried out in a conventional manner. For instance, a tubular reactor is charged with the catalyst and dipped into a sand bath. Usually, sand having a particle size of 60 to 200 mesh is employed as the sand bath. Cold air is blown into the bath from the bottom to control the temperature since the oxidation of p-methoxytoluene is exothermic. The starting material, p-methoxytoluene, is gasified and mixed with air in a vaporizer. Air which is to be mixed with p-methoxytoluene may be diluted with an inert gas such as nitrogen. The mixing ratio of p-methoxytoluene to air is usually determined by taking into consideration is the explosion limit of p-methoxytoluene (about 0.9%), and is preferably from about 0.1% to about 2%. In other words, a p-methoxytoluene gas concentration to air ratio is selected from the range of about 5 to about 100 g./m.$^3$ of air. When occasion demands, a gas concentration of more than 100 g./m.$^3$ of air may be employed. However, when the gas concentration is too high, there is a tendency for the catalytic activity to gradually decrease.

The mixture of the vapor of p-methoxytoluene and air is then passed through the reactor where it comes in contact with the catalyst at a space velocity of about 2,000 to about 12,000 hr.$^{-1}$ In the present invention, the reaction is carried out at a bath temperature of about 430° to about 520° C. Since the oxidation reaction of p-methoxytoluene is an exothermic reaction, the temperature of the catalyst layer is higher than that of the bath temperature and in general the difference between the temperature of the catalyst layer and the bath temperature is at most about 15° to 30° C.

After the reaction is completed, the gaseous mixture is then cooled by a condenser usually at a temperature of 20° to 30° C., and a part of the produced anisaldehyde and the uncoverted p-methoxytoluene is condensed. The gaseous mixture is further passed through an aqueous solution of sodium bicarbonate and an aqueous solution of sodium hydroxide in order to collect anisaldehyde and p-methoxytoluene. The condensate, the aqueous solution of sodium bicarbonate and the aqueous solution of sodium hydroxide are mixed and subjected to extraction with benzene. Anisaldehyde and the unconverted p-methoxytoluene are absorbed into the benzene layer and, by subjecting the benzene layer to rectification, pure anisaldehyde is obtained.

The present invention is more particularly described and explained by means of the following Examples.

EXAMPLE 1

Into 300 ml. of hot water, 7.95 g. of ammonium metavanadate, 3.98 g. of phosphoric acid, 11.82 g. of potassium sulfate and 1.62 g. of copper nitrate were dissolved. To the thus obtained solution, 300 cc. of alumina having an average particle size of 5 mm. was added. After evaporating water with occasional agitation, sintering was carried out at a temperature of 600° C. for 6 hours. The resulting catalyst had the following composition. Catalyst composition (molar ratio):

$V_2O_5 : P_2O_5 : K_2SO_4 : CuO = 1 : 0.6 : 2 : 0.5$

A quartz tubular reactor having an inner diameter of 30.1 mm. was charged with 270 cc. of the obtained catalyst, and dipped in a sand bath. Employing p-methoxytoluene having a purity of 97%, the catalytic oxidation reaction was carried out under the following conditions:

p-Methoxytoluene gas concentration: 47 g./m.$^3$ of air (at 20° C.)
Space velocity: 5,000 hr.$^{-1}$
Bath temperature: 495° C.

Further, catalysts having the composition shown in the following Table 1 were prepared in the same manner as the above except that the amount of potassium sulfate was changed, and the preparation of anisaldehyde was carried out in the same manner as the above.

Table 1

| Run No. | Catalyst composition (molar ratio) | | | | Yield of anisaldehyde (% by weight) |
|---|---|---|---|---|---|
| | $V_2O_5$ | $P_2O_5$ | $K_2SO_4$ | CuO | |
| 1 | 1 | 0.6 | 0 | 0.05 | 39.1 |
| 2 | 1 | 0.6 | 1 | 0.05 | 55.0 |
| 3 | 1 | 0.6 | 2 | 0.05 | 72.5 |
| 4 | 1 | 0.6 | 3 | 0.05 | 55.4 |

EXAMPLE 2

Catalysts having the composition shown in the following Table 2 were prepared in the same manner as in Example 1 except that the amount of copper oxide was changed. Employing the obtained catalysts, anisaldehyde was prepared in the same manner as in Example 1 except that the reaction was carried out at a bath temperature of 490° C.

The results are shown in Table 2.

Table 2

| Run No. | Catalyst composition (molar ratio) | | | | Reaction ratio of p-methoxy-toluene (% by mole) | Yield of anisaldehyde (% by weight) |
|---|---|---|---|---|---|---|
| | $V_2O_5$ | $P_2O_5$ | $K_2SO_4$ | CuO | | |
| 1 | 1 | 0.6 | 2 | 0 | 50.0 | 65.0 |
| 2 | 1 | 0.6 | 2 | 0.05 | 71.5 | 72.5 |
| 3 | 1 | 0.6 | 2 | 0.10 | 74.8 | 65.0 |

EXAMPLE 3

Catalysts having the composition shown in the following Table 3 were prepared in the same manner as in Example 1 except that the amount of diphosphorus pentoxide was changed. Employing the obtained catalysts, anisaldehyde was prepared in the same manner as in Example 1 except that the reaction was carried out at a bath temperature of 460° C.

The results are shown in Table 3.

Table 3

| Run No. | Catalyst composition (molar ratio) | | | | Reaction ratio of p-methoxy-toluene (% by mole) | Yield of anisaldehyde (% by weight) |
| --- | --- | --- | --- | --- | --- | --- |
| | $V_2O_5$ | $P_2O_5$ | $K_2SO_4$ | CuO | | |
| 1 | 1 | 0 | 2 | 0.05 | 90.0 | 5.0 |
| 2 | 1 | 0.2 | 2 | 0.05 | 45.0 | 35.2 |
| 3 | 1 | 0.4 | 2 | 0.05 | 41.0 | 36.0 |
| 4 | 1 | 0.6 | 2 | 0.05 | 37.0 | 38.0 |
| 5 | 1 | 0.8 | 2 | 0.05 | 37.0 | 37.0 |
| 6 | 1 | 1.0 | 2 | 0.05 | 34.0 | 30.0 |

What we claim is:

1. In a process for preparing anisaldehyde by oxidizing p-methoxytoluene in the presnece of a catalyst, the improvement which comprises bringing the vapor of p-methoxytoluene together with an oxidant into contact with a catalyst at a bath temperature of about 430° to about 520° C.; said catalyst consisting esentially of vanadium oxide, about 0.2 to about 0.8 mole of phosphorus oxide per mole of vanadium oxide, about 1.5 to about 2.5 moles of potassium sulfate per mole of vanadium oxide and 0 to about 0.1 moles of copper oxide per mole of vanadium oxide.

2. The process of claim 1, wherein said vanadium oxide is vanadium pentoxide.

3. The process of claim 1, wherein said phosphorus oxide is diphosphorus pentoxide.

4. The process of claim 1, wherein said copper oxide is cupric oxide.

5. The process of claim 1, wherein said oxidant is air.

6. The process of claim 5 wherein said p-methoxytoluene and air are brought into contact with the said catalyst at a gas concentration of about 5 to about 100g./m³. of air at a space velocity of about 2,000 to about 12,000 hr. $^{-1}$

* * * * *